(12) United States Patent
Ben-Haim et al.

(10) Patent No.: US 6,436,095 B1
(45) Date of Patent: Aug. 20, 2002

(54) METHOD FOR MONITORING REVASCULARIZATION TREATMENT USING PRE-PMR DATA AND POST-PMR DATA

(75) Inventors: Shlomo Ben-Haim, Haifa; Uri Yaron, Zichron-Yaacov; Joel Zilberstein, Haifa, all of (IL)

(73) Assignee: Biosense, Inc., New Brunswick, NJ (US)

(*) Notice: Subject to any disclaimer, the term of this patent is extended or adjusted under 35 U.S.C. 154(b) by 91 days.

(21) Appl. No.: 09/689,257

(22) Filed: Oct. 12, 2000

Related U.S. Application Data

(63) Continuation of application No. 09/142,696, filed as application No. PCT/IL97/00307 on Sep. 15, 1997, now Pat. No. 6,200,310, which is a continuation-in-part of application No. PCT/IL97/00011, filed on Jan. 8, 1997.

(51) Int. Cl.[7] ................................................ A61B 18/18
(52) U.S. Cl. ......................... 606/10; 606/15; 607/122; 607/101; 604/95.01
(58) Field of Search .............................. 606/10–16, 41, 606/45–50; 607/89, 101, 102, 122; 604/95.01, 95.05

(56) References Cited

U.S. PATENT DOCUMENTS

| | | |
|---|---|---|
| 4,658,817 A | 4/1987 | Hardy |
| 4,788,975 A | 12/1988 | Shturman et al. |
| 5,125,924 A | 6/1992 | Rudko |
| 5,125,926 A | 6/1992 | Rudko et al. |
| 5,188,111 A | 2/1993 | Yates et al. |
| 5,350,375 A | 9/1994 | Deckelbaum et al. |
| 5,380,316 A | 1/1995 | Aita et al. |
| 5,389,096 A | 2/1995 | Aita et al. |
| 5,391,199 A | 2/1995 | Ben-Haim |
| 5,403,311 A | 4/1995 | Abele et al. |
| 5,403,356 A | 4/1995 | Hill et al. |
| 5,431,168 A | 7/1995 | Webster, Jr. |
| 5,433,198 A | 7/1995 | Desai |

(List continued on next page.)

FOREIGN PATENT DOCUMENTS

| | | |
|---|---|---|
| WO | WO94/06349 A1 | 3/1994 |
| WO | WO95/07657 A1 | 3/1995 |
| WO | WO96/05768 A1 | 2/1996 |
| WO | WO97/24983 A2 | 7/1997 |
| WO | WO97/25101 A2 | 7/1997 |
| WO | WO97/29803 A1 | 8/1997 |

OTHER PUBLICATIONS

Mirhoseini et al.; "Transmyocardial Laser Revascularization: A Review", J. of Clinical Laser Medicine & Surgery vol. 11, No. 1, 1993; pp. 15–19.

Bonn; "High–power lasers help the ischaemic heart"; The Lancet (Science and Medicine) vol. 348, 7/96; p. 118.

Lee et al.; "Effects of laser irradiation delivered by flexible fiberoptic system on the left ventricular internal myocardium"; Brief Communications, vol. 106, No. 3, 9/83 American Heart Journal (from Cardiac Center, Cedars Medical Center; and the University of California at Davis); pp. 587–590.

May; "Photonic Approaches to Burn Diagnostics"; Biophotonics International, May/Jun. 1995, vol. 2, No. 3; pp. 44–50.

Primary Examiner—Roy D. Gibson
(74) Attorney, Agent, or Firm—Louis J. Capezzuto

(57) ABSTRACT

A method for monitoring revascularization treatment provided to tissue, such as heart tissue, comprises the steps of identifying a location in tissue and positioning a catheter at the location. Electrical signals of the tissue are measured in order to establish pre-revascularization data wherein the pre-revascularization data is stored. Energy is imparted to the tissue with the catheter in order to create a channel in the tissue at the location. Electrical signals of the tissue are measured after creation of the channel in order to establish post-revascularization data. The pre-revascularization data and the post-revascularization data are compared in order to determine successful treatment to the tissue.

15 Claims, 11 Drawing Sheets

U.S. PATENT DOCUMENTS

| | | |
|---|---|---|
| 5,450,846 A | 9/1995 | Goldreyer |
| 5,462,544 A * | 10/1995 | Saksena et al. ............. 600/373 |
| 5,487,391 A | 1/1996 | Panescu |
| 5,554,152 A | 9/1996 | Aita et al. |
| 5,566,673 A | 10/1996 | Shiono et al. |
| 5,568,809 A * | 10/1996 | Ben-haim ................... 600/433 |
| 5,607,421 A | 3/1997 | Jeevanandam et al. |
| 5,651,786 A | 7/1997 | Abela et al. |
| 5,724,975 A | 3/1998 | Negus et al. |
| 5,738,096 A | 4/1998 | Ben-Haim |
| 5,769,843 A * | 6/1998 | Abela et al. ................ 600/424 |
| 5,824,005 A * | 10/1998 | Motamedi et al. .......... 600/374 |
| 5,840,031 A | 11/1998 | Crowley |
| 5,871,495 A | 2/1999 | Mueller |
| 5,885,272 A | 3/1999 | Aita et al. |
| 5,891,133 A | 4/1999 | Murphy-Chutorian |
| 5,893,848 A | 4/1999 | Negus et al. |
| 5,964,757 A | 10/1999 | Ponzi |
| 6,023,638 A | 2/2000 | Swanson |
| 6,024,739 A | 2/2000 | Ponzi et al. |
| 6,027,473 A | 2/2000 | Ponzi |

\* cited by examiner

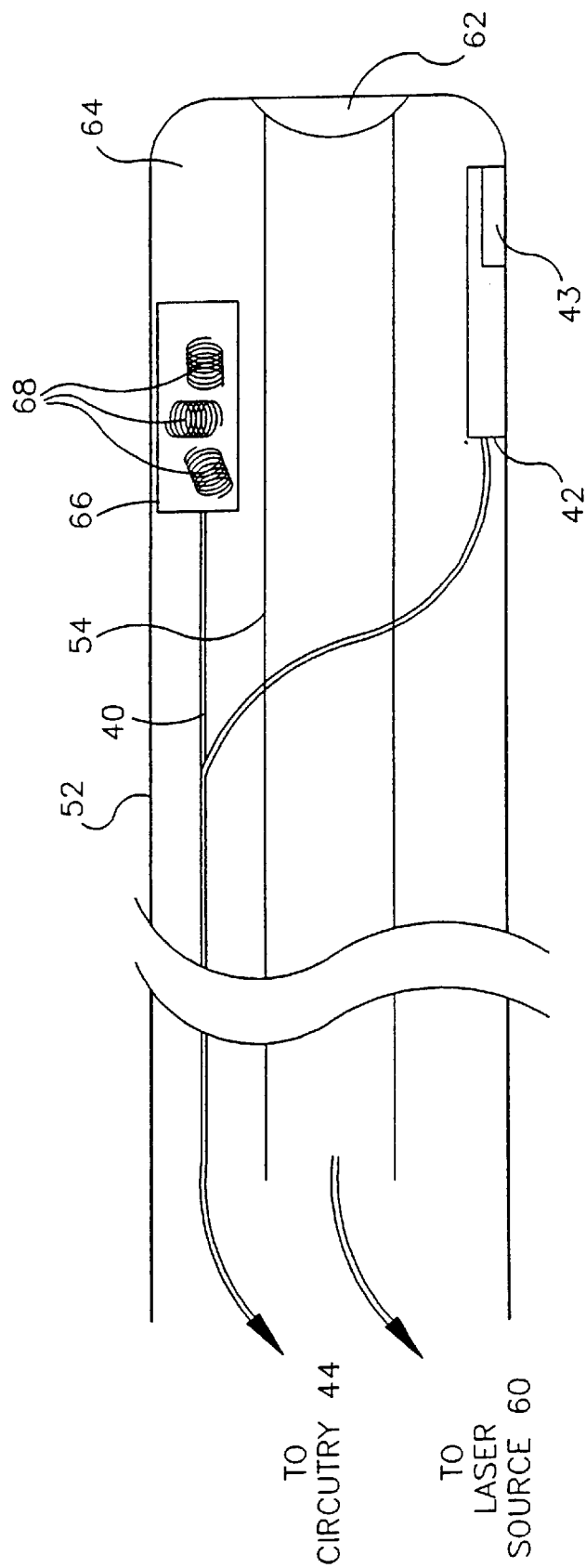

METHOD FOR MONITORING REVASCULARIZATION TREATMENT USING PRE-PMR DATA AND POST-PMR DATA

RELATED APPLICATION

This is a Continuation of prior application Ser. No.: 09/142,696, filed Dec. 7, 1998, now U.S. Pat. No. 6,200,310 which is a 371 of PCT/IL97/00307 filed Sep. 15, 1997, which is a continuation-in-part of PCT patent application no. PCT/IL97/00011, filed Jan. 8, 1997, which is incorporated herein by reference.

FIELD OF THE INVENTION

The present invention relates generally to methods and devices for cardiac surgery, and specifically to methods and apparatus for myocardial revascularization.

BACKGROUND OF THE INVENTION

Myocardial revascularization is a technique, known in the art, for creating channels in ischemic heart tissue to improve the blood supply to ischemic myocardium. It may be performed by various techniques, the best-known of which is laser myocardial revascularization, which employs laser radiation for generating such channels.

In transmyocardial revascularization (TMR), as is known in the art, a computer-controlled laser is used to drill penetrating holes about 1 mm in diameter in the myocardium by delivering laser energy to the epicardium through an incision in the chest and the pericardium. Blood at the outer, epicardial openings of the channels typically clots after a few minutes, but the inner portions of the channels, communicating with the ventricle, remain patent. It is hypothesized that during systole, blood flows through these channels into naturally-existing myocardial sinusoids, supplementing the impaired arterial blood supply.

According to another hypothesis, the local injury caused to the myocardium by various forms of energy (e.g., laser radiation, as described above, or alternatively, RF radiation, or ultrasonic or mechanical energy) stimulates local angiogenesis, eventually supplementing the impaired arterial blood supply. Although there are no conclusive answers at present regarding the underlying mechanism, there is clinical evidence of the treatment's therapeutic efficacy.

U.S. Pat. No. 5,389,096, to Aita, et al., which is incorporated herein by reference, describes methods and apparatus for percutaneous myocardial revascularization (PMR). A deflectable, elongated lasing apparatus is guided to an area within the patient's heart, and the distal end of the apparatus is directed to an area of interest in the inner wall of the heart. The wall is irradiated with laser energy to form channels therein, preferably without perforating the epicardium. Alternatively, PMR may be carried out by applying other energy forms, as described above, from inside the art.

In TMR, as is known in the art, the channels are created through the myocardium from the outside in, and the transient blood stream ensuing upon channel completion constitutes an intrinsic indication of successful drilling. In PMR, however, the channel is generated from inside the heart chamber and, preferably, does not penetrate the myocardium. Consequently there is no direct indication of successful generation of the channel.

A PMR procedure, whether employing laser energy or any other suitable energy form, may fail due to a multiplicity of reasons. For example, referring specifically to laser PMR, the catheter inserted into the heart may be incorrectly oriented, so that the energy does not impact and penetrate the endocardium, or does not penetrate to a significant depth. Alternatively, the distal end of the catheter may be obstructed, for example, by a thrombus and/or ablated tissue residues. Because systems for PMR known in the art do not give any indication of whether the energy pulse has successfully generated a channel in the myocardium, it is difficult or impossible for an interventional cardiologist to detect and correct such a failure during the procedure.

SUMMARY OF THE INVENTION

It is an object of some aspects of the present invention to provide a reliable indication as to whether an energy pulse locally imparted to the heart has successfully produced a channel in the myocardium.

It is a further object of some aspects of the present invention to provide methods and apparatus for monitored PMR.

In the context of the present patent application and in the claims, the term "PMR" is taken to refer to any and all techniques of percutaneous myocardial revascularization treatment, including laser, RF, ultrasound and mechanical methods, but not limited thereto. Accordingly, while preferred embodiments of the present invention are described herein largely in terms of creating channels in the myocardium using laser irradiation, those skilled in the art will understand that the principles of the present invention are similarly applicable to other PMR techniques.

Some aspects of the present invention are based on the finding by the inventors that when an energy pulse is incident on the myocardium in such a manner as to create a channel therein, it causes detectable variations in the heart's electrical activity, both local and global. In particular, the applicants have observed such variations when a laser beam creates a channel in the myocardium.

The local variation is expressed in the form of an elevated ST segment in the locally-measured electrogram. The elevated ST is characteristic of injuries to the heart, and is observed to last for at least several minutes after generating the channel. It is a distinctly local effect, and is not observed outside a diameter of several millimeters (typically 3 mm) from the point at which the channel is generated.

The global variation is observed in the form of disturbance of the heart's sinus rhythm, typically in one or more ventricular premature beats (VPB's) immediately following the laser pulse. The VPB's are observed both in electrogram signals recorded within the heart chamber and in ECG signals recorded on the body surface.

It is still another object of some aspects of the present invention to provide indication that the channels have been generated in accordance with predetermined dimensions, location and orientation. These aspects of the invention are based primarily on the ability of ultrasonic waves to resolve zones of differing tissue characteristics, in particular density, thus imaging the channels' dimensions and direction.

Other aspects of the present invention use real-time sensing technologies, particularly based on optical sensing, for detecting local changes in blood perfusion. By comparing pre- and post-PMR optical signals, enhanced blood perfusion of ischemic zones, due to successful channel generation, may be observed.

Some preferred embodiments of the present invention are based on a PMR catheter as described in PCT patent application no. PCT/IL97/00011, filed Jan. 14, 1997, which is assigned to the assignee of the present patent application, and whose disclosure is incorporated herein by reference. The catheter comprises a waveguide, for conveying energy to the endocardium, preferably laser energy, and has at least one sensor at its distal tip. The sensor may comprise one or more electrophysiological sensing electrodes, position sensors, ultrasound transducers, or other sensors known in the art.

In some of these preferred embodiments, the sensor comprises an electrode, which receives electrical signals from the heart indicative of the efficacy of local PMR treatment, i.e., whether an energy pulse or series of pulses has actually succeeded in generating a channel of substantial depth in the myocardium. The catheter is coupled to signal processing circuitry, which processes the signals received by the electrode and provides an indication to a user of the catheter, typically an interventional cardiologist, as to whether the channel has been generated. The indication is typically based on elevation of the ST segment and/or VPB's in the local electrogram during at least several minutes after the channel has been generated. Failure to sense such a change after one or several energy pulses is taken to be an indication of an error or malfunction, requiring the cardiologist's intervention. Preferably, the catheter is held in place at a candidate site for a period both before and after channel generation, long enough to gather pre- and post-PMR electrograms, which are compared to ascertain the efficacy of the local treatment.

Preferably, the elevated ST effect, which is of a highly localized nature and significantly long duration, also provides an indication to the user during subsequent PRM channel generation as to whether a channel preexists in a new candidate area.

In some of these preferred embodiments, the electrode is used for gating the energy source, as described in PCT patent application no. PCT/IL97/00011, mentioned above, as well as sensing signals indicative of successful channel generation.

In some preferred embodiments of the present invention, ECG is measured during the PMR procedure by means of skin electrodes. Disturbances of the normal sinus rhythm, particularly ventricular premature beats (VPB's), are sensed as an indication that an energy pulse has successfully generated a channel in the myocardium. Absence of such disturbance is, similarly, taken to indicate error or malfunction.

In other preferred embodiments of the present invention, the sensor at the distal end of the catheter comprises an ultrasonic transducer. The transducer generates signals responsive to the changes induced in the myocardial tissue by the channel generation operation. The signals are used to detect successful generation of the channel, alone or in conjunction with internal or external ECG readings.

Preferably, the ultrasonic signals are further used to monitor the depth and/or direction of the channel generated by the radiation.

In further preferred embodiments of the present invention, the sensor at the distal end of the catheter comprises a blood flow sensor, preferably an optical sensor or, alternatively, an ultrasonic sensor, which generates signals responsive to local microcirculation blood flow. The signals are used to detect successful reperfusion at the treated site.

In alternative preferred embodiments of the present invention, the sensor at the distal end of the catheter comprises an optical sensor, which receives light emitted by endocardial tissue. Light is transmitted from a radiation source, optionally via the waveguide in the catheter, as described above, to the myocardial tissue. The radiation is tuned to be absorbed by substances in the tissue related to local blood perfusion and stimulate them to fluoresce (i.e., autofluorescence). The emitted autofluorescent radiation is received by the optical imaging sensor and is measured to detect successful channel generation. For example, the sensor may be used to detect local NADH levels, which are correlated with ischemia, as described in a series of publications, including Kedem et al., Q. J. Exp. Physiol. 66:501–514, 1981; Furman et al., Cardiovasc. Res. 10:606–612, 1985; and Duboc et al., Lancet, Aug. 30 1986, p. 522, which are incorporated herein by reference.

Alternatively, fluorescing contrast agents, known in the art, such as fluorescein or indocyanine green (ICG), may be injected into the blood stream to facilitate photo-detection of local blood perfusion by angiography. Such methods are described, for example, in U.S. Pat. No. 5,566,673, to Shiono, and in an article by May in Biophotonics International, May/June 1995, pp. 44–50, which are incorporated herein by reference.

Although preferred embodiments are described herein with reference to certain types of PMR catheters, in particular those described in the above-mentioned PCT patent application no. PCT/IL/00011, it will be appreciated that the principles of the present invention may similarly be applied using other types of catheters and apparatus, as are known in the art. In particular, as noted above, the catheter may comprise a device for imparting to the heart energy forms other than laser radiation, for example, RF, ultrasonic or mechanical energy.

There is thus provided, in accordance with a preferred embodiment of the present invention, apparatus for PMR treatment, including:

an elongate probe having a distal end for engaging heart tissue of a subject, and including a revascularization device, which imparts energy to the heart tissue for generating perfusion-enhancing channels therein; and a sensor, which provides an indication responsive to the treatment.

Preferably, the sensor receives signals generated by the body of the subject responsive to the treatment.

Further preferably, the sensor includes an electrode, which is positioned on the probe adjacent the distal end thereof.

Alternatively or additionally, the electrode is placed on the subject's body independently of the probe.

In preferred embodiments, the sensor includes a transducer, preferably an ultrasonic transducer, which generates signals indicative of the treatment.

Alternatively or additionally, the sensor includes a blood flow sensor, which generates signals responsive to microcirculation.

Preferably, the transducer is positioned on the probe adjacent the distal end thereof.

In another preferred embodiment, the sensor includes an optical sensor, and the apparatus preferably includes a waveguide, which transmits fluorescence-stimulating radiation to the myocardial tissue, wherein the sensor receives fluorescence emitted from the tissue and generates signals indicative of the treatment.

Preferably the apparatus includes signal processing circuitry, which is coupled to the sensor and analyzes the signals to provide an indication of the efficacy of the treatment. Preferably, the circuitry detects an elevated ST segment or, alternatively or additionally, an arrhythmia. Preferably, the arrhythmia detected by the circuitry includes at least one VPB.

Alternatively or additionally, the circuitry detects a change in tissue characteristics adjacent to the distal end of the probe. Preferably, the change includes a change in tissue density, or, alternatively or additionally, an increase in blood perfusion adjacent to the distal end of the probe.

Preferably, the revascularization device applies laser radiation to the heart tissue.

Alternatively, the revascularization device applies RF energy, high-intensity ultrasonic radiation, and/or mechanical energy to the heart tissue.

There is also provided, in accordance with a preferred embodiment of the present invention, a method for monitored PMR treatment of the heart of a subject, including:

bringing a probe, including a revascularization device for imparting energy to the heart, into engagement with heart tissue of a subject;

imparting energy to the heart tissue using the device so as to generate perfusion-enhancing channels therein; and receiving a signal from the body of the subject responsive to the treatment.

Preferably, receiving the signal includes receiving a signal generated by the body of the subject indicative of successful performance of the treatment.

Further preferably, sensing the signal includes sensing an electrical signal inside the heart of the subject, or, alternatively or additionally, on a surface of the body of the subject.

In a preferred embodiment, receiving the signal includes receiving energy reflected from the heart tissue, preferably ultrasonic energy reflected from a designated channel location within the heart.

In another preferred embodiment, receiving energy includes receiving fluorescence radiation emitted from the heart tissue, preferably autofluorescent radiation or, alternatively, from an agent administered into the subject's blood stream.

In still another preferred embodiment, receiving the signal includes receiving signals responsive to microcirculation blood flow rate adjacent a designated channel location within the heart.

Preferably, the above method includes processing the signals to provide an indication of the efficacy of the treatment, most preferably by detecting an elevated ST segment, or alternatively or additionally, by detecting an arrhythmia. Preferably, detecting the arrhythmia includes detecting a VPB.

In a preferred embodiment, processing the signals includes detecting changes in tissue characteristics in the channel area, preferably detecting changes in tissue density.

Alternatively, processing the signals includes detecting changes in blood perfusion in the tissue, preferably, detecting an enhancement of the perfusion.

Preferably, imparting energy to the heart includes imparting laser radiation.

Alternatively, imparting energy to the heart includes imparting RF radiation, high-intensity ultrasonic radiation, or mechanical energy.

The present invention will be more fully understood from the following detailed description of the preferred embodiments thereof, taken together with the drawings in which:

BRIEF DESCRIPTION OF THE DRAWINGS

FIG. 2B is a schematic illustration showing details of the distal end of the catheter of FIG. 2A, in accordance with a preferred embodiment of the present invention;

DETAILED DESCRIPTION OF PREFERRED EMBODIMENTS

Figure 1A:
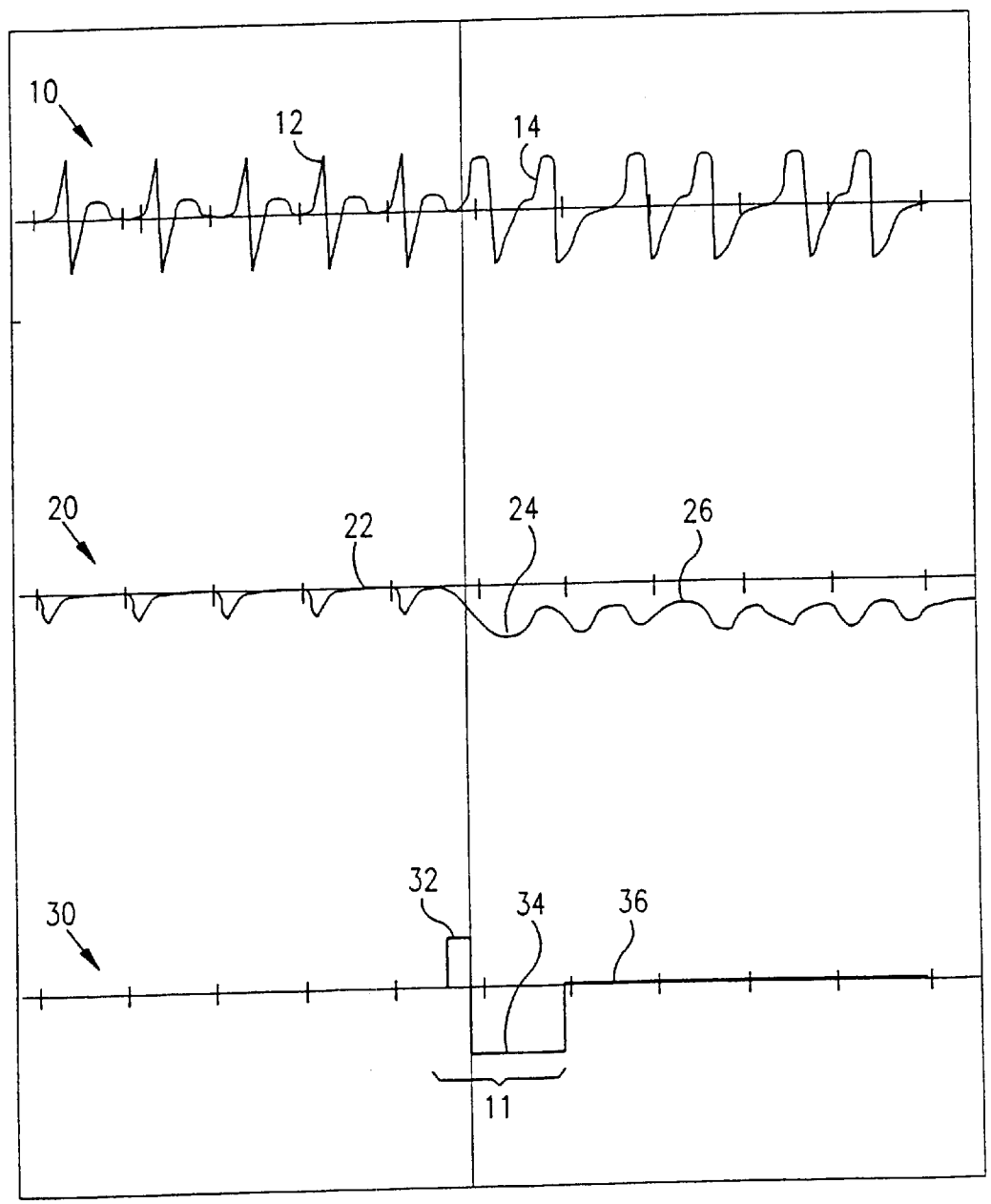
FIG. 1A is a schematic illustration showing electrical signals received from the body of a subject before, during and after PRM laser firing.
Figure 1B:
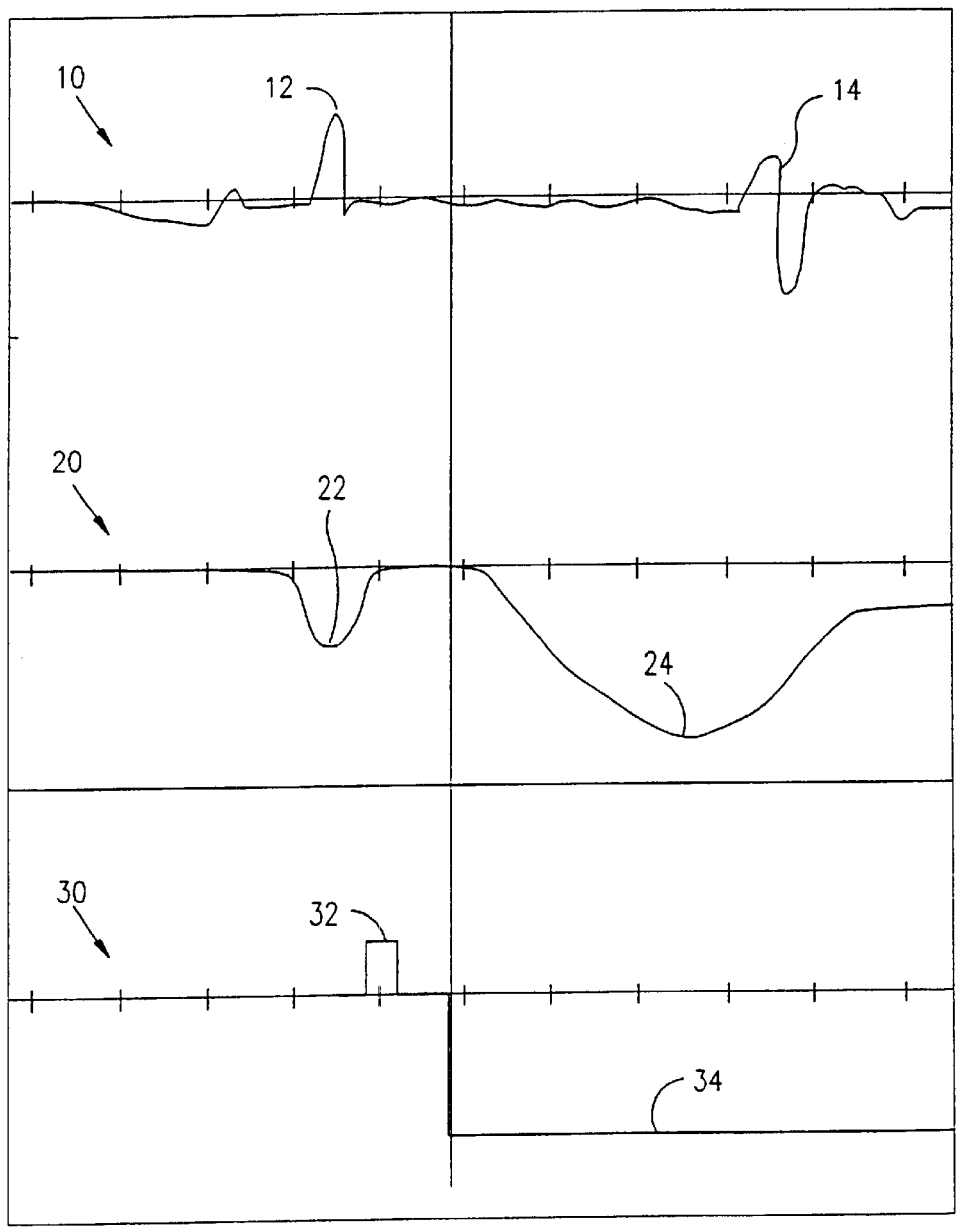
FIG. 1B is a schematic illustration showing the signals of FIG. 1A on an expanded time scale.

Reference is now made to FIGS. 1A and 1B, which are graphs schematically depicting signals received from the body of a dog undergoing an experimental PMR treatment, using a laboratory system similar to that which is shown schematically in FIG. 2A below and described with reference thereto.

The traces in FIGS. 1A and 1B represent ECG signals 10 received from body surface electrodes, intracardiac electrogram signals 20 received from an electrode on a PMR catheter, as described below, and a trigger pulse 30 applied to a laser source used in performing the PMR treatment. FIG. 1B shows a portion 11 of the traces of FIG. 1A on an expanded time scale.

As shown in the figures, it has been found that injury to the heart tissue due to PMR drilling induces specific local and global variations in the electrical activity of the heart. The local variation manifests itself in the form of an elevated ST segment 24 in locally-measured electrogram 20, which was found to last for several minutes after PMR drilling.

The global variation is observed as a disturbance of the heart's normal sinus rhythm, typically in the form of one or more ventricular premature beats (VPB's) 14 in ECG trace 10 and electrogram trace 20, immediately following the laser pulse.

In the course of experiments performed on 25 dogs, elevated ST segments were observed after at least 60% of the PMR laser pulses and VPB's were observed after at least 95% of the PMR laser pulses administered to the dogs. These variations in the heart's normal electrical activity were found to correlate with successful PMR drilling. The elevated ST segments are considered by the applicants more reliable in this respect, due to the lesser number of false positives encountered. When either the elevated ST segment or VPB's were not observed following a laser pulse, it was found that a channel had not been generated, i.e., no false negatives were encountered.

Figure 2A:
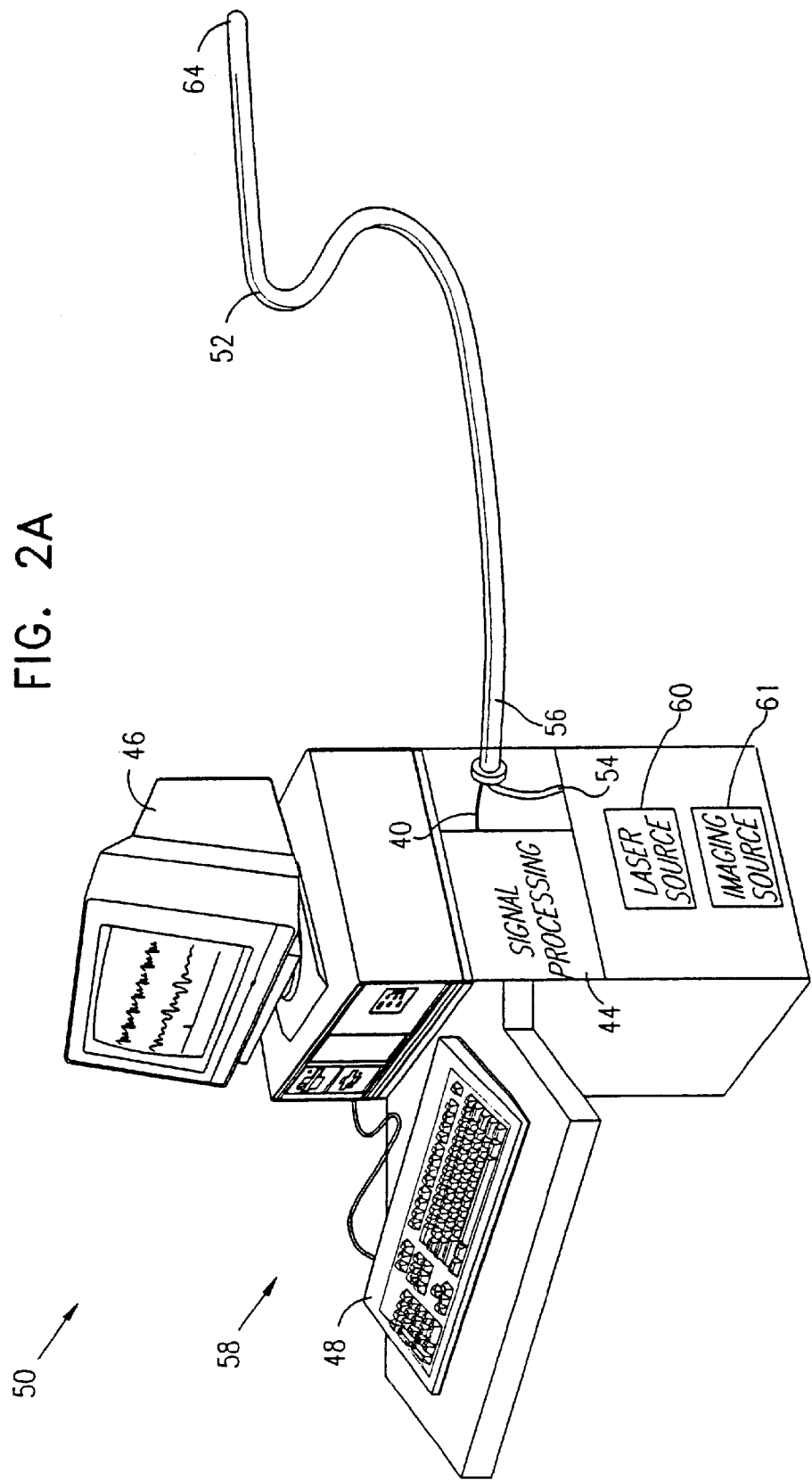
FIG. 2A is a schematic illustration of a catheter system for use in PMR, in accordance with a preferred embodiment of the present invention.

Reference is now made to FIGS. 2A and 2B, which schematically illustrate a system 50 for PMR, including a catheter 52 for insertion into the body of a subject, in accordance with a preferred embodiment of the present invention. Catheter 52 comprises an optical waveguide 54, as is known in the art, for transmitting laser energy from the laser source to the heart tissue. A focusing lens 62 at distal end 64 of catheter 52 focuses the laser radiation from waveguide 54 into heart tissue. Catheter 52 is connected at its proximal end 56 to a console 58, which includes a laser source 60 optically coupled to waveguide 54. The laser is activated to generate PMR channels into the heart tissue. Optionally, console 58 includes an optical radiation source 61, which is used in conjunction with a catheter comprising an optical sensor for measuring local blood perfusion (as shown in detail in FIG. 7B and described with reference thereto).

Preferably, console 58 also includes signal processing circuitry 44, as well as a display 46 and user controls 48. Preferably, intracardiac electrogram trace 10, the skin ECG trace 20 and/or the laser trigger signal 30 are monitored and displayed on display 46 during the PMR treatment. As described above, these traces provide a real-time visual indication to the user of the catheter, typically an interventional cardiologist, as to whether the channel has been generated.

Additionally or alternatively, the signal processing circuitry analyzes the data and gives the user a "go/no go" indication as to whether the channel has been successfully generated.

Catheter 52 preferably also includes a position sensor 66, fixed in a known position adjacent distal end 64, for use in navigating and positioning the catheter within the heart, as described more fully in PCT patent application no. PCT/IL97/00011, incorporated herein by reference.

As shown in FIG. 2B, catheter 52 includes a sensor unit 42 at its distal end 64. Preferably, sensor unit 42 comprises an electrode 43 for sensing electrical potentials in heart tissue adjacent to distal end 64. Local electrogram signals from electrode 43 are conveyed by wires 40 to circuitry 44. Preferably, these signals are used to monitor the changes in the electrogram signals due to the PMR drilling, as described above, thus indicating successful channel drilling. The electrogram signals may also be used to trigger laser source 60, as disclosed in PCT patent application no. PCT/IL97/00011, mentioned above.

Although catheter system 50 is shown and described with reference to electrode 43, it will be understood that sensor unit 42 may include other sensors and other types of elements. For example, additional electrodes may be placed at or adjacent to distal end 64, either on catheter 52 itself or on a structure fixed to the catheter, as described in PCT patent application no. PCT/IL97/00009, filed Jan. 8, 1997, which is assigned to the assignee of the present patent application, and whose disclosure is incorporated herein by reference.

Figure 3A:
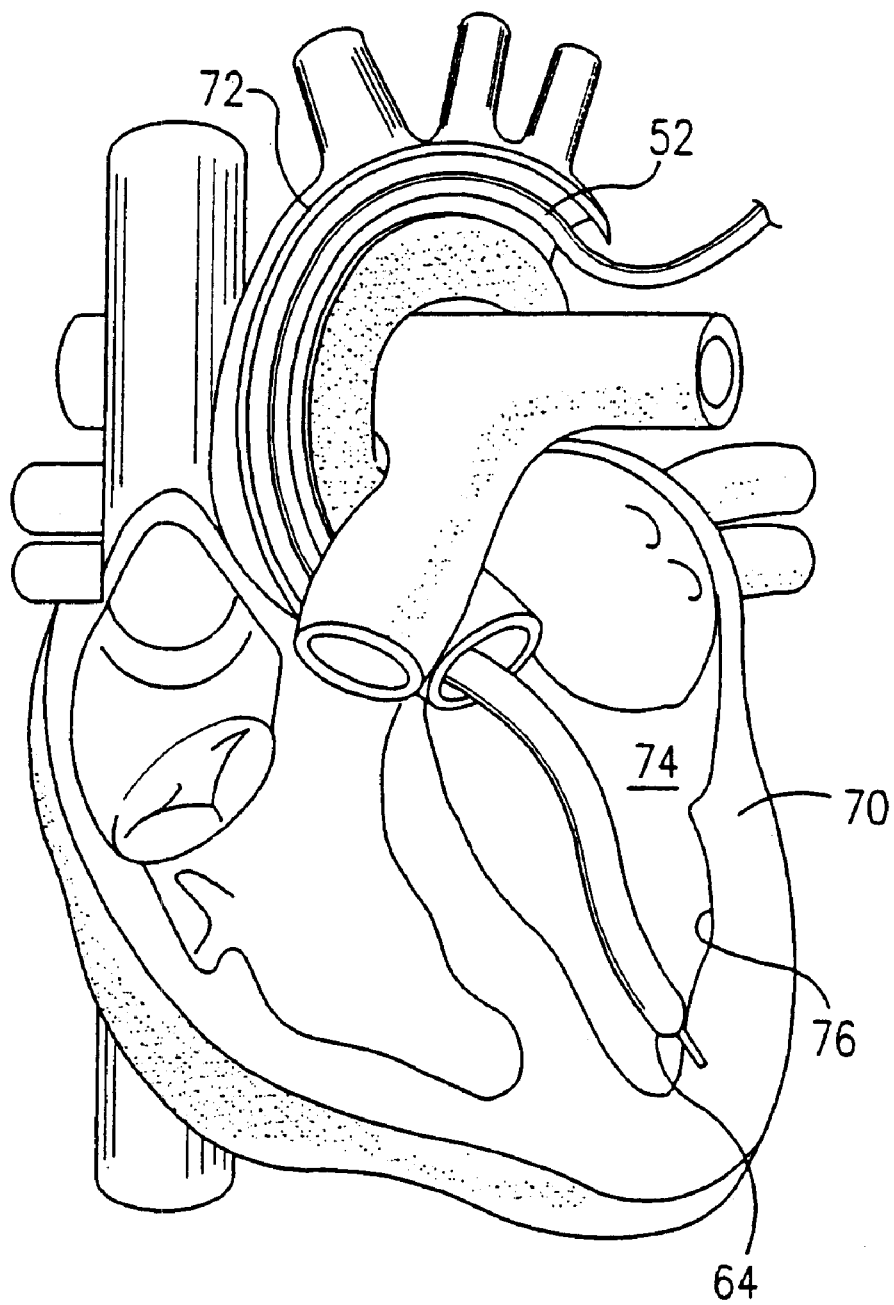
FIG. 3A is a schematic, sectional illustration of a human heart, into which the catheter of FIGS. 2A and 2B is inserted for performing a PMR procedure therein, in accordance with a preferred embodiment of the present invention.

FIG. 3A is a schematic, sectional illustration showing catheter 52 inserted into heart 70 of a subject, in accordance with a preferred embodiment of the present invention. Catheter 52 is fed percutaneously into the subject's vascular system, for example, through the femoral artery, and is passed through aorta 72 into left ventricle 74 of heart 70. Distal end 64 is positioned against endocardium 76 in a desired position and orientation and drills channels therein, preferably, as described in the above-mentioned PCT patent application no. PCT/IL97/00011.

Figure 3B:
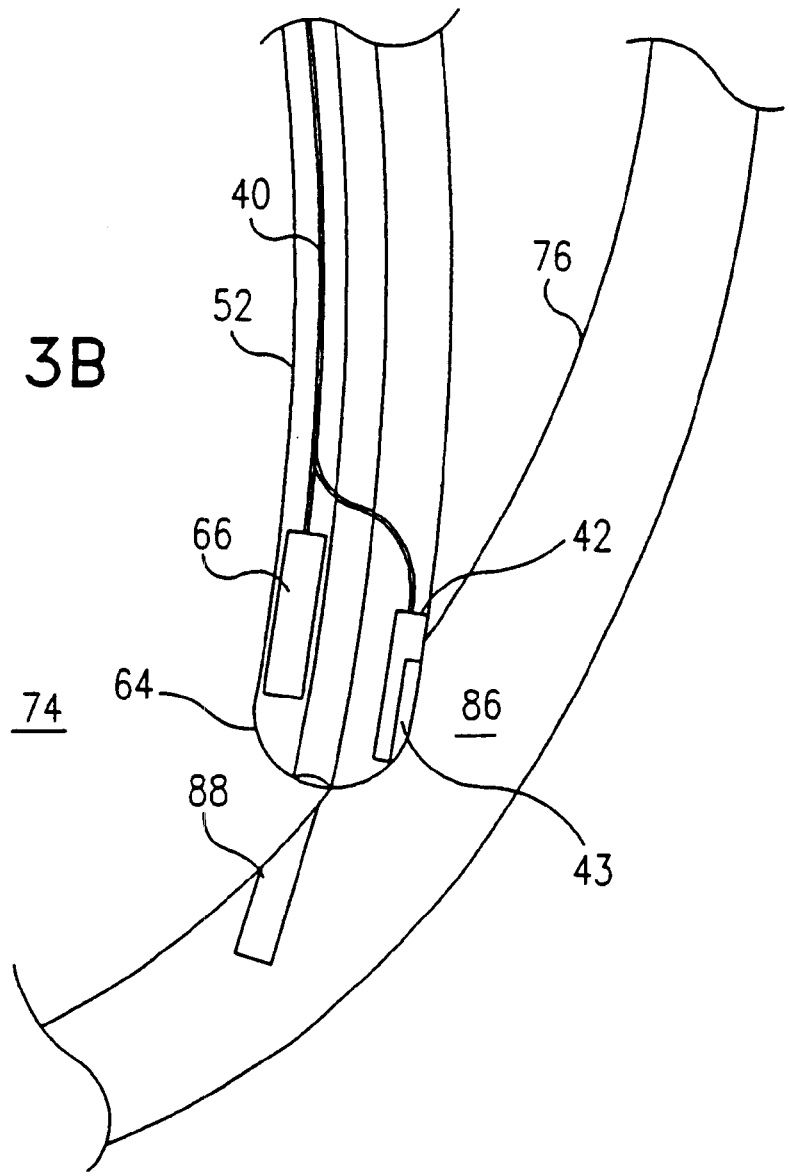
FIG. 3B is a schematic, sectional detail illustration showing a channel drilled in the tissue of the heart of FIG. 3A, in accordance with a preferred embodiment of the present invention.

FIG. 3B is a schematic, sectional illustration showing details of catheter 52 drilling a channel 88 in myocardium 86 of heart 70, in accordance with a preferred embodiment of the present invention. Electrode 43 measures the local electrical signals prior to, during and after the drilling to assess successful drilling, as described above.

Figure 4:
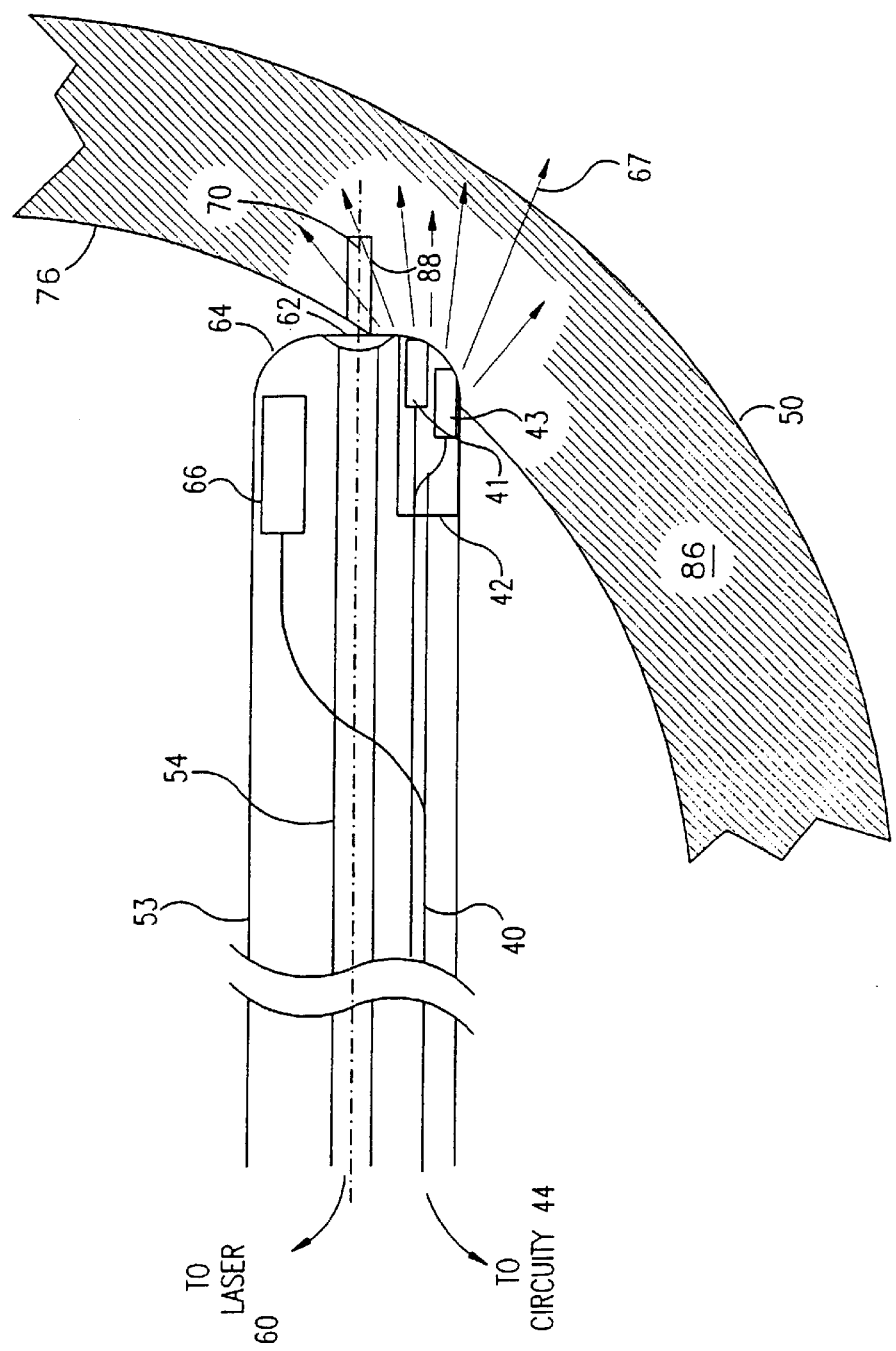
FIG. 4 is a schematic illustration showing details of the distal end of a catheter for PMR, in accordance with an alternative preferred embodiment of the present invention.

FIG. 4 is a schematic illustration showing details of another catheter 53 for use in PMR, in accordance with alternative preferred embodiments of the present invention. Catheter 53 includes waveguide 54, lens 62 and position sensor 66, and is coupled to console 58, substantially as described above with reference to catheter 52. Additionally, sensor unit 42 of catheter 53 includes an ultrasound transducer 41. Preferably, transducer 41 comprises a transducer array, as is known in the art, which emits a beam 67 that may be steered over a range of angles within an area distal to distal end 64 of catheter 53. Transducer 41 is coupled via wires 40 to signal processing circuitry 44.

Catheter 53 is preferably brought into contact with endocardium 76, as shown in FIG. 4. Preferably, signals received by circuitry 44 from transducer 41 are used to map the designated channel location prior to and after the PMR procedure to determine, by means of comparison, the dimensions, location and orientation of channel 88, thus indicating its successful generation.

Alternatively or additionally, the ultrasonic readings may be used for dynamic monitoring of channel parameters. Preferably, following each pulse or several pulses of the laser source, the transducer signals are used to measure the depth and direction of channel 88 and determine whether the optimal, desired depth has been reached and whether catheter 53 is properly aimed.

In some preferred embodiments of the present invention, transducer 41 and electrode 43 are used in tandem for assessing successful completion of the PMR procedure, by combining data regarding variations in the electrogram signals following PMR drilling with quantitative measurement of dimensional parameters of channel 88.

Although in the embodiments described above, catheters 52 and 53 include various sensors and optical elements in certain preferred combinations and configurations, it will be appreciated that in other preferred embodiments of the present invention, PRM catheters may include some or all of these sensors and elements in other combinations and in the same or other configurations. Such catheters may also include other types of sensors known in the art, for example, temperature or pressure sensors, useful in diagnosing other aspects of cardiac function.

They may further include blood flow sensors for measuring the local microcirculation flow rate, or optical sensors for visualizing local blood perfusion by tissue autofluorescence or angiography enhanced by fluorescing contrast agents.

Figure 5:
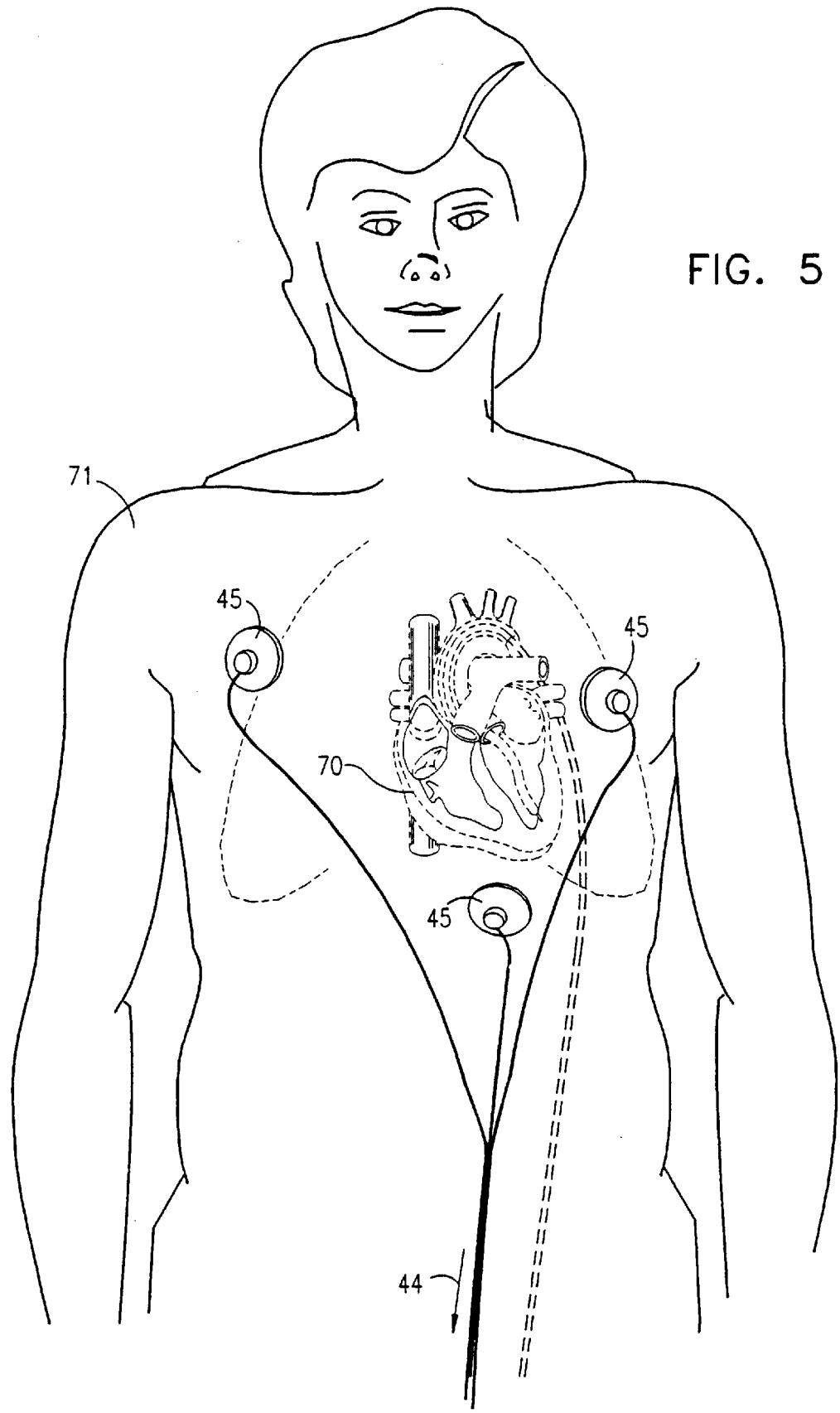
FIG. 5 is a schematic illustration of a human body and heart, into which the catheter of FIGS. 2A and 2B is inserted to perform a PMR procedure therein, in accordance with another preferred embodiment of the present invention.

FIG. 5 is a schematic illustration showing the use of skin electrodes 45 placed on a subject's body 71 to record ECG signals therefrom during a PMR procedure, in accordance with a preferred embodiment of the present invention. Preferably, electrodes 45 record the skin ECG signals prior to and for several minutes after laser firing to assess successful drilling, primarily by observing VPB's, as described above with reference to FIGS. 1A and 1B.

In some preferred embodiments of the present invention, the global changes sensed by skin electrodes 45 may serve as the sole indication of successful drilling.

Alternatively, in other preferred embodiments of the present invention, the global variations monitored in the ECG signals are used in conjunction with local variations in the electrical signals sensed by electrode 43.

Further alternatively or additionally, in some preferred embodiments, the signals measured by electrodes 45 may be used in conjunction with measurements from ultrasonic transducer 41, as described above with reference to FIG. 4.

Figure 6:
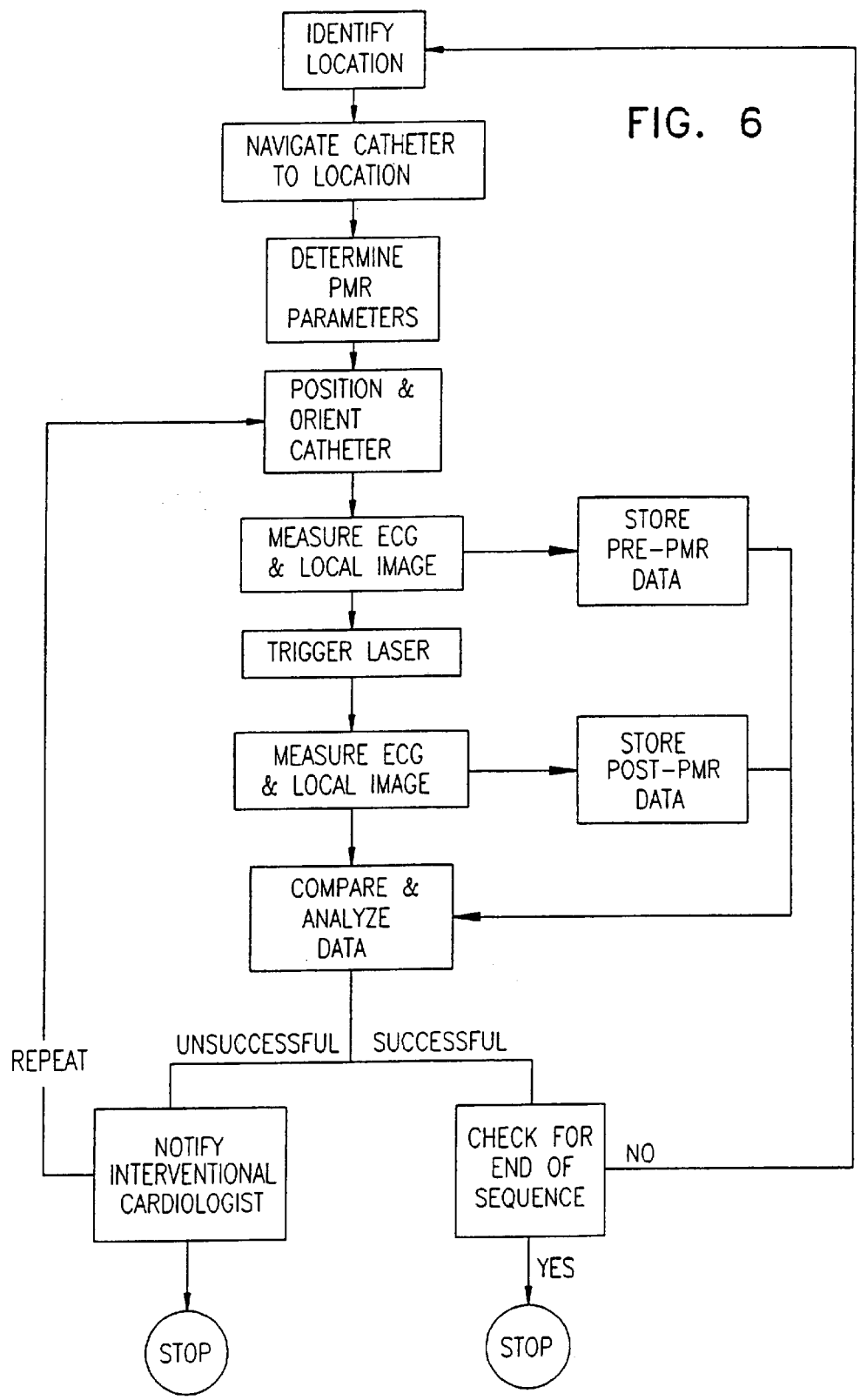
FIG. 6 is a flowchart illustrating a method of monitored PMR, in accordance with a preferred embodiment of the present invention.

FIG. 6 is a flow chart that summarizes the key steps in a method for monitored PMR, in accordance with preferred embodiments of the present invention. The method is described below with reference to catheter 52, shown in FIGS. 2A and 2B, but it will be understood that the principles of this method may be applied using other suitable catheters, as described hereinabove.

Prior to beginning PMR, at least one candidate area for the procedure is identified within heart 70, preferably as described in the above-mentioned PCT patent application no. PCT/IL97/00011.

Catheter 52 is then navigated to the candidate area. The position and orientation of distal end 64 of the catheter are preferably ascertained and controlled by receiving signals from position sensor 66, and are compared with a stored map of the heart, although such position and orientation sensing are not a necessary part of the present invention. When the distal end is suitably positioned and oriented, intracardiac electrogram signals are received and stored by console 48. Laser source 60 is fired to drill a channel in the heart tissue, as described above. Following the laser firing, post-PMR readings are taken by electrode 43 and analyzed, preferably by comparing them with the pre-PMR signals, for indication of successful drilling. The position of the channel is marked on the map, and catheter 52 is then repositioned to drill the next channel. This procedure is preferably repeated until channels have been drilled to a desired density over the entire candidate area.

It will be understood that as described above, the method of monitored PMR shown in FIG. 6 may similarly be implemented by monitoring the skin surface ECG or by using ultrasound or other sensing modalities. Similarly, the PMR procedure may be carried out using other methods of PMR, such as RF or mechanical methods, mentioned above, in place of the laser.

Figure 7A:
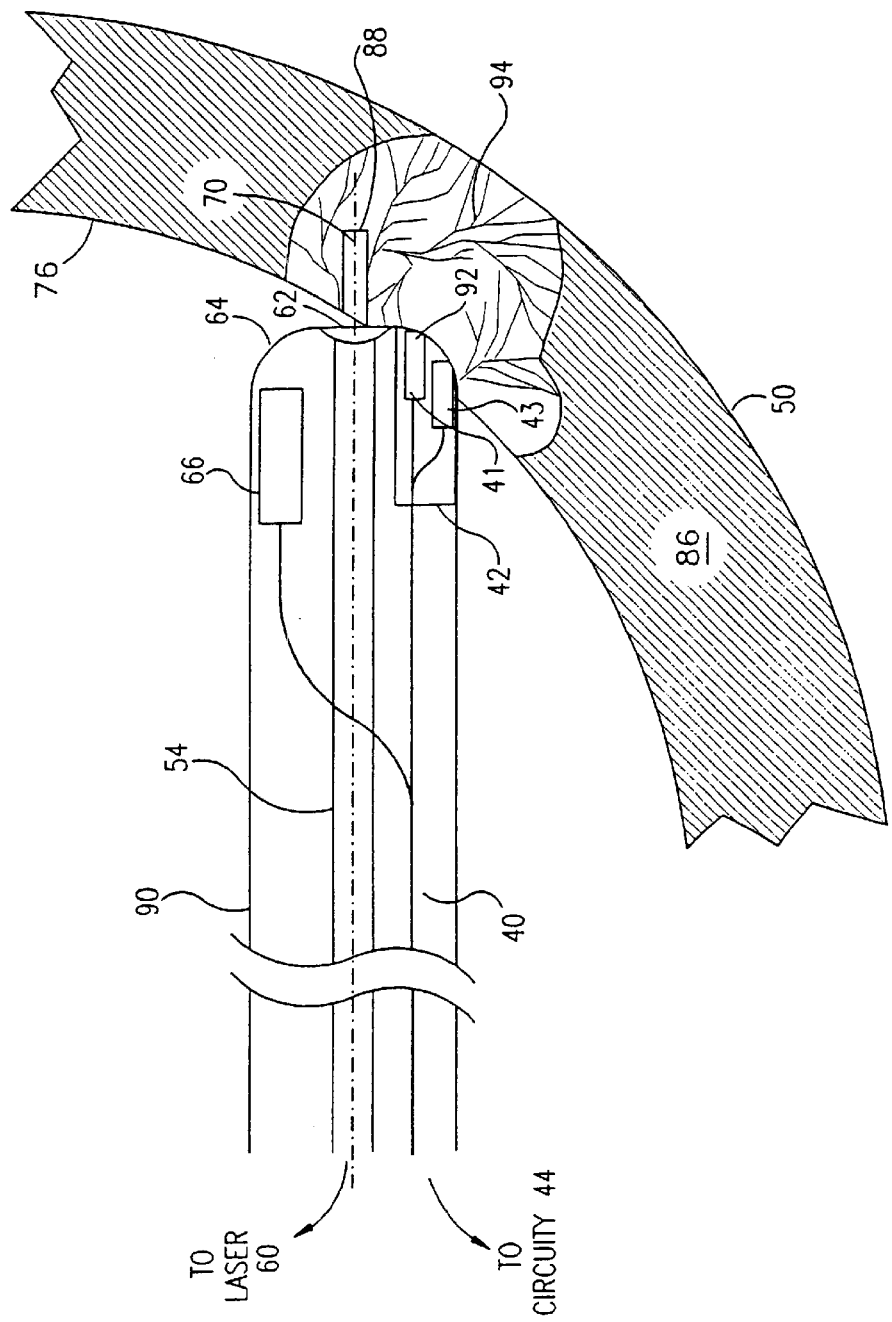
FIG. 7A is a schematic illustration showing details of the distal end of a catheter for PMR, in accordance with an alternative preferred embodiment of the present invention.

Reference is now made to FIG. 7A, which is a schematic illustration showing details of a catheter 90 for use in monitored PMR, in accordance with an alternative preferred embodiment of the present invention. Catheter 90 includes waveguide 54, lens 62 and position sensor 66, and is coupled to console 58, substantially as described above with reference to catheter 52. Additionally, sensor unit 42 of catheter 90 includes a blood flow sensor 92, which senses signals responsive to blood flow within microvasculature 94 in a vicinity of channel 88, generated by the catheter.

Sensor 92 preferably comprises an optical detector, which senses microperfusion and/or tissue oxygenation based on light reflected from the heart tissue. For example, the sensor may be used to detect NADH activity, as described in the above-mentioned articles by Kedem, Furman and Duboc, or to detect the concentration of a contrast agent or fluorescent marker. Alternatively, sensor 92 may comprise an ultrasound transducer. Sensor 92 is coupled via wires 40 to circuitry 44.

When catheter 90 is brought into contact with endocardium 76, sensor 92 receives signals from the vicinity of channel 88. Signals prior to and after the PMR procedure are compared, so as to detect changes in local blood flow in the vicinity. An enhancement of the local blood flow following the procedure, indicated by increased microperfusion and/or tissue oxygenation, is generally a sign of successful channel generation.

Figure 7B:
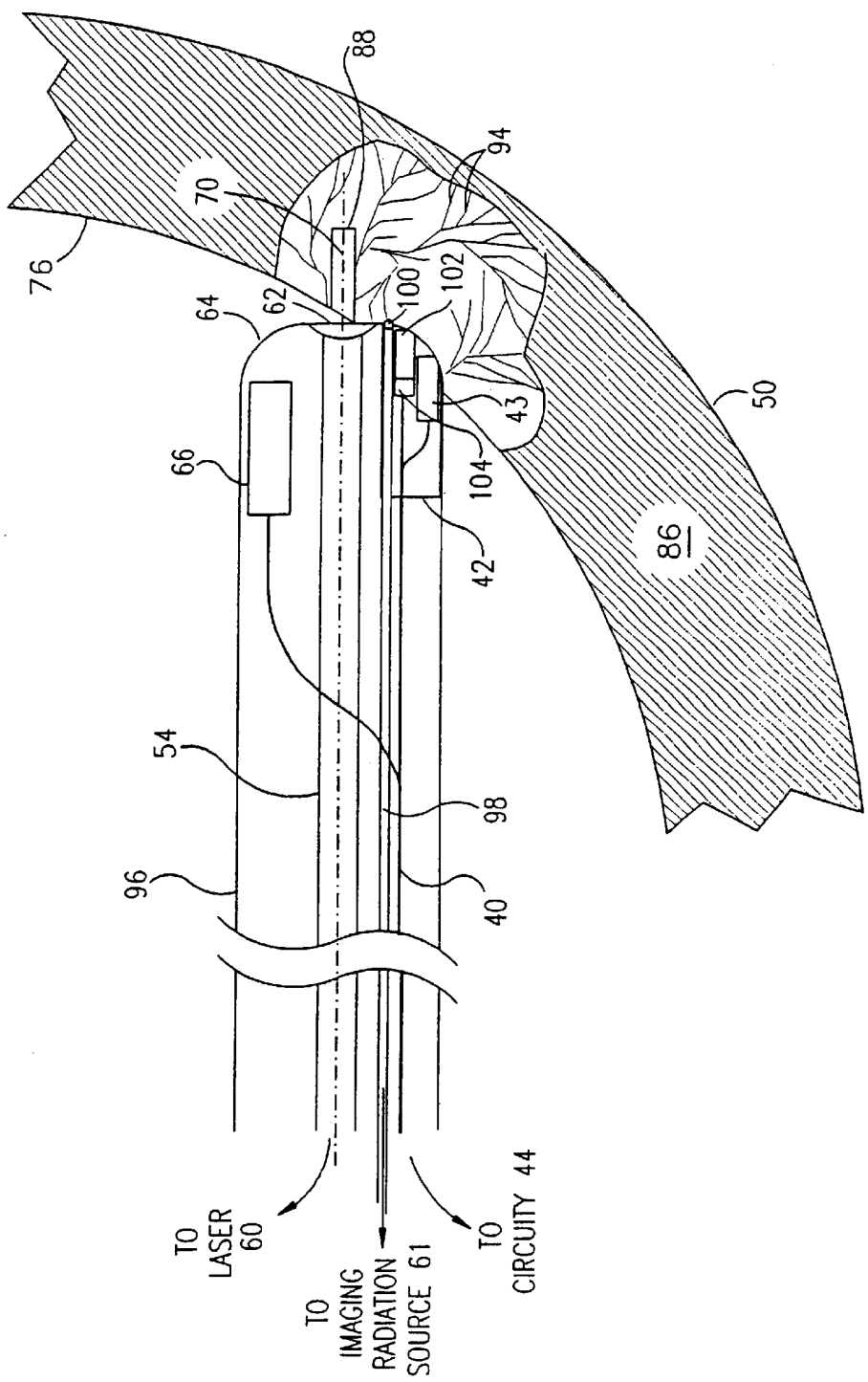
FIG. 7B is a schematic illustration showing details of the distal end of a catheter for PMR, in accordance with yet another preferred embodiment of the present invention.

FIG. 7B schematically illustrates a catheter 96, similar in design and function to catheter 90 described above, in accordance with another preferred embodiment of the present invention. Sensor unit 42 of catheter 96 includes an optical sensor assembly 102, comprising a waveguide 99, which is connected to radiation source 61 (shown in FIG. 2A) and transmits fluorescence-stimulating radiation to the myocardial tissue through a lens 100. Assembly 102 further comprises a light detector 104, connected via wires 40 to circuitry 44. Detector 104 receives fluorescent radiation emitted from the tissue and generates signals in response thereto. For example, the detector may detect near-IR fluorescence of ICG injected into the patient's bloodstream and conveyed thereby to microvasculature 94, as described in the above-mentioned article by May. Preferably, detector 104 includes an optical filter, as is known in the art, so that the detector receives radiation only in a wavelength band of interest.

When catheter 96 is brought into contact with the endocardium, sensor assembly 102 receives signals in the vicinity of channel 88 prior and after the PMR procedure to determine changes in local perfusion, as explained above. Increased perfusion generally indicates a successful PMR treatment.

It will be appreciated that the principles and methods of the present invention may be applied using catheters and apparatus of other types known in the art, to generate channels 88. These channels may be drilled using a laser source, as described above, or alternatively, using drills of other suitable types known in the art, for example, a high-speed roto-ablator drill head. Alternatively, the channels may be produced using a focused, high-intensity beam of ultrasonic radiation, or by applying RF energy to the tissue. Although in the preferred embodiments described above, catheters 52, 53, 90 and 96 are used to produce channels in the wall of left ventricle 74, it will also be understood that the principles of the present invention may be applied to assess the efficacy of PMR procedures applied to other parts of the heart.

It is believed that other physiological parameters may also be affected by PRM channel generation in the heart. It will therefore be evident to those skilled in the art that the principles of the present invention may be applied using other types of sensors, as appropriate, to provide signals responsive to channel generation.

It will be appreciated that the preferred embodiments described above are cited by way of example, and the full scope of the invention is limited only by the claims.

What is claimed is:

1. A method for monitoring revascularization treatment provided to tissue comprising the steps of:

identifying a location in tissue;

positioning a catheter at the location;

measuring electrical signals of the tissue in order to establish pre-revascularization data;

storing the pre-revascularization data;

imparting energy to the tissue with the catheter in order to create a channel in the tissue at the location;

measuring electrical signals of the tissue after creation of the channel in order to establish post-revascularization data, and comparing the pre-revascularization data to the post-revascularization data in order to determine successful treatment to the tissue.

2. The method according to claim 1, further comprising creating a map based on the pre-revasculatization data.

3. The method according to claim 2, further comprising creating another map based on the post-revascularization data.

4. The method according to claim 3, wherein the maps are created based on the electrical signals of the tissue.

5. The method according to claim 3, wherein the maps are created using ultrasound.

6. The method according to claim 1, further comprising storing the post-revascularization data.

7. The method according to claim 1, wherein the tissue is heart tissue.

8. The method according to claim 7, further comprising measuring electrical signals with the catheter.

9. The method according to claim 7, further comprising measuring electrical signals with a surface ECG.

10. The method according to claim 7, further comprising navigating the catheter with a position sensor.

11. The method according to claim 10, further comprising orienting the catheter at the location.

12. The method according to claim 1, wherein the energy is laser energy.

13. The method according to claim 1, wherein the energy is RF energy.

14. The method according to claim 1, wherein the energy is ultrasound energy.

15. The method according to claim 1, wherein the energy is mechanical energy.

* * * * *

UNITED STATES PATENT AND TRADEMARK OFFICE
CERTIFICATE OF CORRECTION

PATENT NO.     : 6,436,095 B1
DATED          : August 20, 2002
INVENTOR(S)    : Ben-Haim et al.

It is certified that error appears in the above-identified patent and that said Letters Patent is hereby corrected as shown below:

<u>Column 11,</u>
Line 5, "pre-revasculatization" should be -- pre-revascularization --.

Signed and Sealed this

Second Day of September, 2003

JAMES E. ROGAN
*Director of the United States Patent and Trademark Office*